United States Patent
Mukaide et al.

(10) Patent No.: US 8,638,903 B2
(45) Date of Patent: Jan. 28, 2014

(54) X-RAY IMAGING APPARATUS AND METHOD OF X-RAY IMAGING

(75) Inventors: Taihei Mukaide, Atsugi (JP); Kazuhiro Takada, Kawasaki (JP); Kazunori Fukuda, Fujisawa (JP); Masatoshi Watanabe, Isehara (JP)

(73) Assignee: Canon Kabushiki Kaisha, Tokyo (JP)

( * ) Notice: Subject to any disclaimer, the term of this patent is extended or adjusted under 35 U.S.C. 154(b) by 423 days.

(21) Appl. No.: 12/993,083

(22) PCT Filed: Jan. 15, 2010

(86) PCT No.: PCT/JP2010/050748
§ 371 (c)(1),
(2), (4) Date: Nov. 16, 2010

(87) PCT Pub. No.: WO2010/082687
PCT Pub. Date: Jul. 22, 2010

(65) Prior Publication Data
US 2011/0103549 A1 May 5, 2011

(30) Foreign Application Priority Data
Jan. 15, 2009 (JP) .................................. 2009-006862
Nov. 19, 2009 (JP) .................................. 2009-264411

(51) Int. Cl.
*G03H 5/00* (2006.01)
*G01N 23/04* (2006.01)

(52) U.S. Cl.
USPC ................................. 378/36; 378/62; 378/159

(58) Field of Classification Search
USPC ................................. 378/36, 37, 62, 156, 159
See application file for complete search history.

(56) References Cited

U.S. PATENT DOCUMENTS 5,199,057 A * 3/1993 Tamura et al. ................. 378/43
5,881,126 A * 3/1999 Momose ........................ 378/36

(Continued)

FOREIGN PATENT DOCUMENTS

JP 2002-102215 A 4/2002
WO 2008/029107 A2 3/2008

OTHER PUBLICATIONS

Pfeiffer et al., "Phase retrieval and differential phase-contrast imaging with low-brilliance X-ray sources", Nature Physics, Nature Publishing Group, London-GB LNKD, Mar. 26, 2006, pp. 258-261.

(Continued)

*Primary Examiner* — Thomas R Artman
(74) *Attorney, Agent, or Firm* — Canon USA, Inc. IP Division (57) ABSTRACT

Provided is an X-ray imaging apparatus and a method of X-ray imaging, with which the apparatus can be reduced in size and a differential phase image or a phase image with consideration of an X-ray absorption effect of an object can be obtained.

X-rays are spatially split, and a first attenuation element in which the transmission amount of X-rays continuously changes in accordance with the displacement when the X-rays pass through an object is used. Transmittance is calculated by using the first attenuation element and a second attenuation element that is different from the first attenuation element with respect to an amount of change or a characteristic of change in the transmission amount of X-rays in a direction of a displacement of the X-rays. A differential phase image and the like of the object are calculated using the transmittance.

13 Claims, 7 Drawing Sheets

(56) References Cited

U.S. PATENT DOCUMENTS

| | | | |
|---|---|---|---|
| 6,885,503 B2* | 4/2005 | Yun et al. | 359/565 |
| 7,412,024 B1 | 8/2008 | Yun et al. | |
| 7,787,588 B1* | 8/2010 | Yun et al. | 378/43 |
| 7,920,673 B2* | 4/2011 | Lanza et al. | 378/62 |
| 8,036,336 B2* | 10/2011 | Mukaide et al. | 378/53 |
| 8,214,158 B2* | 7/2012 | Mukaide et al. | 702/28 |
| 2010/0054415 A1 | 3/2010 | Olivo et al. | |
| 2010/0278304 A1* | 11/2010 | Mukaide et al. | 378/53 |
| 2010/0318302 A1* | 12/2010 | Mukaide et al. | 702/28 |
| 2011/0064196 A1* | 3/2011 | Mukaide et al. | 378/62 |
| 2011/0103549 A1* | 5/2011 | Mukaide et al. | 378/62 |
| 2011/0158389 A1* | 6/2011 | Mukaide et al. | 378/62 |
| 2012/0294421 A1* | 11/2012 | Mukaide et al. | 378/62 |
| 2012/0321042 A1* | 12/2012 | Watanabe et al. | 378/62 |

OTHER PUBLICATIONS

Kagoshima et al., "Scanning differential-phase-contrast hard X-ray microscopy with wedge absorber detector", Japanese Journal of Applied Physics, vol. 43, No. 11A, Nov. 1, 2004, pp. L1449-L1451.

* cited by examiner

X-RAY IMAGING APPARATUS AND METHOD OF X-RAY IMAGING

TECHNICAL FIELD

The present invention relates to an X-ray imaging apparatus and a method of X-ray imaging.

BACKGROUND ART

Nondestructive testing using electromagnetic radiation is used for a variety of industrial applications and medical applications. X-rays are electromagnetic waves having a wavelength in the range of, for example, about 1 pm to 10 nm ($10^{-12}$ to $10^{-8}$ m). X-rays having a short wavelength (energy of about 2 keV or larger) are called hard X-rays, and X-rays having a long wavelength (energy in the range of about 0.1 keV to about 2 keV) are called soft X-rays.

For example, an absorption contrast method obtains an absorption image of an object by using the difference in transmittance of X-rays passing through the object. Because X-rays easily penetrate through an object, the absorption image is used for internal crack detection of steel materials and for security purposes such as baggage inspection.

On the other hand, an X-ray phase imaging method detects a phase shift of X-rays caused by an object. The X-ray phase imaging method is effective for an object made of a material having a small density difference, because absorption contrast of X-rays is not clear for such a material. For example, the X-ray phase imaging method can be used for imaging of polymer blends or for medical applications.

Patent Literature 1 discloses a very convenient and effective method of X-ray phase imaging that uses a refraction effect due to phase shift of X-rays caused by an object. To be specific, the method uses a microfocus X-ray source and utilizes an effect that the edge of an object is detected in an enhanced manner owing to a refraction effect of X-rays caused by the object when the distance between the object and a detector is large. Because the method uses the refraction effect, it is not necessary to use highly coherent X-rays such as synchrotron radiation, which distinguishes the method from many other X-ray phase imaging methods.

Patent Literature 2 discloses an imaging apparatus having a mask that blocks X-rays on an edge portion of the pixel of the detector. By setting the mask so that a part of the mask is irradiated with X-rays when an object is not present, a displacement of X-rays due to a refraction effect caused by the object can be detected as a change in intensity.

CITATION LIST

Patent Literature

PTL 1 Japanese Patent Laid-Open No. 2002-102215
PTL 2 International Publication No. WO2008/029107

SUMMARY OF INVENTION

Technical Problem

However, in order to obtain an edge-enhanced image of an object by using the method described in Patent Literature 1, it is necessary that the distance between the object and the detector be sufficiently large with consideration of the size of a pixel of the detector, because the refraction angle due to the refraction effect of X-rays caused by the object is very small. Therefore, the method described in Patent Literature 1 requires a large apparatus.

In contrast, the distance between an object and a detector may be small with the method described in Patent Literature 2, so that a small apparatus can be used. However, because a mask that blocks X-rays is provided, a displacement of X-rays incident on the blocking mask cannot be detected. That is, high-precision analysis is difficult because an insensitive region exists.

Moreover, the methods described in the Patent Literature 1 and Patent Literature 2 have a problem in that an absorption effect of X-rays and a phase effect of X-rays cannot be separated from each other if an object absorbs a large amount of X-rays.

The present invention provides an X-ray imaging apparatus and a method of X-ray imaging for obtaining a differential phase image or a phase image with consideration of an absorption effect of X-rays caused by the object, in which the size of the apparatus can be made smaller than that of the method described in Patent Literature 1, and with which an analysis having a precision higher than that of the method described in Patent Literature 2 can be performed.

Solution to Problem

An X-ray imaging apparatus according to an aspect of the present invention includes a splitting element that spatially splits X-rays generated by an X-ray generator; a first attenuation element on which X-rays split by the splitting element are incident; a second attenuation element on which X-rays split by the splitting element are incident, the second attenuation element being disposed adjacent to the first attenuation element; and a detecting unit configured to detect intensities of X-rays that have passed through the first attenuation element and the second attenuation element, wherein the first attenuation element and the second attenuation element are configured so that a transmission amount of X-rays continuously changes in accordance with a position at which the X-rays are incident, and wherein the first attenuation element and the second attenuation element are different from each other with respect to an amount of change or a characteristic of change in a transmission amount of X-rays in a direction of a displacement of the X-rays.

A method of X-ray imaging used in an X-ray imaging apparatus, the method according to an aspect of the present invention, includes generating X-rays; spatially splitting the X-rays; making X-rays that have been spatially split be incident on a first attenuation element and a second attenuation element, the second attenuation element being disposed adjacent to the first attenuation element; detecting intensities of X-rays that have passed through the first attenuation element and the second attenuation element; and calculating a differential phase image or a phase image of an object using an X-ray transmittance, the X-ray transmittance being calculated from the intensities of X-rays that have been detected, wherein the first attenuation element and the second attenuation element are configured so that a transmission amount of X-rays continuously changes in accordance with a position at which the X-rays are incident, and wherein the first attenuation element and the second attenuation element are different from each other with respect to an amount of change or a characteristic of change in the transmission amount of X-rays in a direction of a displacement of the X-rays.

Advantageous Effects of Invention

The present invention provides an X-ray imaging apparatus and a method of X-ray imaging that can obtain a differential phase image or a phase image with consideration of an absorption effect of X-rays caused by the object, in which the size of the apparatus can be made smaller than that of Patent Literature 1, and with which an analysis having a precision higher than that of Patent Literature 2 can be performed.

DESCRIPTION OF EMBODIMENTS

Hereinafter, X-ray imaging apparatuses according to embodiments of the present invention will be described. Each of the apparatuses uses a phase shift of X-rays caused by an object, and is capable of obtaining a more precise differential phase image and a more precise phase image of an object even if the object has a high absorptance of X-rays.

To be specific, the apparatus converts a displacement of the incident position of X-rays, which is due to the refraction effect of the X-rays caused by an object, into intensity information of the X-rays and thereby detects the displacement. At this time, first attenuation elements each having an absorptance gradient (transmittance gradient) and second attenuation elements disposed adjacent to the first attenuation elements are used.

An attenuation element having an absorptance gradient (transmittance gradient) refers to an element in which the amount of X-rays absorbed (transmitted) continuously changes in accordance with the incident position of the X-rays. The attenuation element can be made by changing the shape continuously or stepwise. Alternatively, the attenuation element can be made by changing an amount of X-rays absorbed (transmitted) per unit volume continuously or stepwise. In this description, the term "continuously" may include the meaning of "stepwise".

The first attenuation element and the second attenuation element are different from each other with respect to the amount of change and the characteristic of change in the transmission amount of X-rays in the direction of a displacement of the X-rays. For example, if a position at which X-rays are incident changes between a state in which an object is present and a state in which an object it not present, the first attenuation element is configured so that the transmission amount of X-rays decreases and the second attenuation element is configured so that the transmission amount of X-rays increases.

By using these elements, absorption information and phase information can be independently obtained. Using the absorption information, a more precise differential phase image and a more precise phase image can be obtained. Specific description will be given below.

First Embodiment

An X-ray imaging apparatus according to a first embodiment obtains a transmittance image from a change in the absorption of X-rays, that is, from a change in the transmittance of X-rays. Moreover, the X-ray imaging apparatus obtains a differential phase image and a phase image from a phase shift of X-rays.

Figure 1:
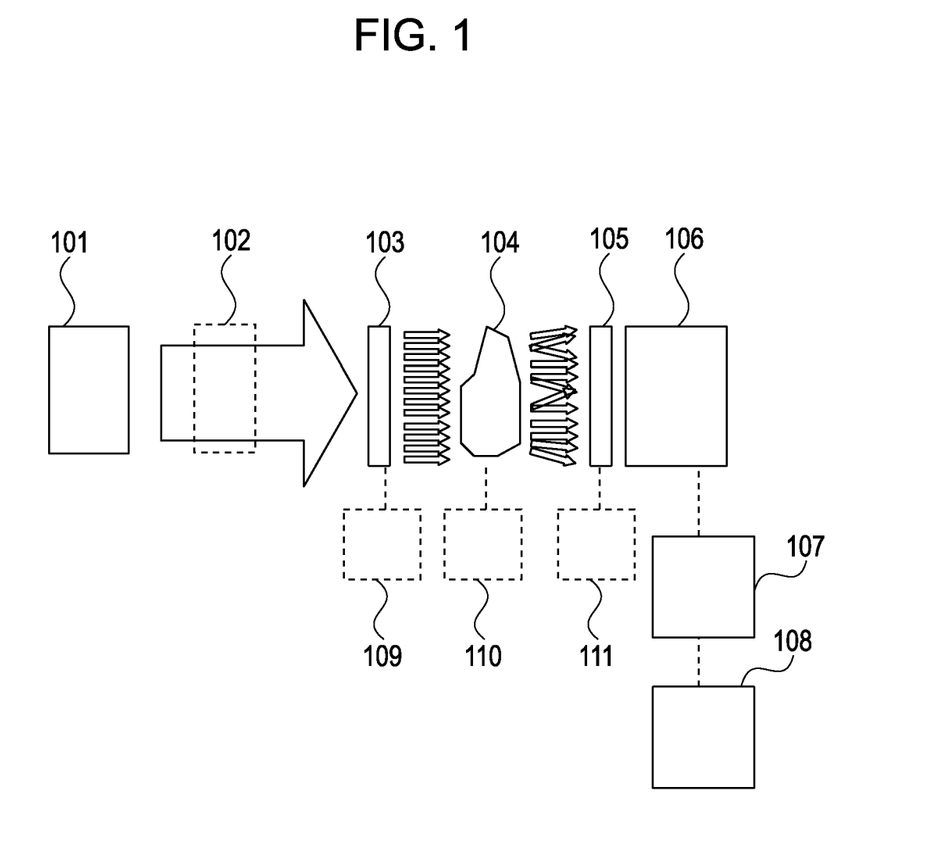
FIG. 1 is a schematic view of an apparatus according to first and second embodiments.

FIG. 1 is a schematic view of an X-ray imaging apparatus according to the first embodiment. An X-ray source 101 generates X-rays. On the optical path of the X-rays, a splitting element 103, an object 104, an attenuation unit 105, and a detector 106 are disposed. Movement units 109, 110, and 111 that use stepping motors or the like may be additionally provided so as to move the splitting element 103, the object 104, and the attenuation unit 105. The object 104 can be appropriately moved so that an image of a specific position of the object 104 can be obtained. X-rays that have been generated by the X-ray source 101 are spatially split by the splitting element 103. That is, the splitting element 103 serves as a sample mask having a plurality of apertures described in Patent Literature 2, and the X-rays that have passed through the splitting element 103 become a bundle of X-rays. The splitting element 103 may have a slit array with a pattern of lines and spaces, or may have holes that are arranged two-dimensionally.

As long as X-rays can pass through the slits in the splitting element 103, it is not necessary that the slits extend through the substrate of the optical element. The material of the splitting element 103 can be selected from substances having a high X-ray absorptance, such as Pt, Au, Pb, Ta, and W.

The intervals between lines and spaces of the X-rays, which have been split by the splitting element 103, at the position of the detector 106 are equal to or larger than the pixel size of the detector 106. That is, the size of pixels that constitute an X-ray intensity detecting unit is equal to or smaller than the spatial period of the X-rays at the position of the detector 106.

The object 104 absorbs the sheet-shaped X-rays that have been spatially split by the splitting element 103, changes the phases of the X-rays, and refracts the X-rays. The X-rays that have been refracted are incident on the attenuation unit 105. The detector 106 detects the intensities of the X-rays that have passed through the attenuation unit 105. A calculating unit 107 numerically processes the information about the X-rays obtained by the detector 106, and outputs the result of the processing to a display unit 108.

Examples of the object 104 include a human body, an inorganic material, and an inorganic-organic composite material.

The detector 106 can be selected from, for example, an X-ray flat panel detector, an X-ray CCD camera, and a direct-conversion-type two-dimensional X-ray detector. The detector 106 may be disposed adjacent to the attenuation unit 105, or disposed at a distance from the attenuation unit 105. Alternatively, the attenuation unit 105 may be incorporated in the detector 106.

In order to use monochromatic X-rays, a monochromatizing unit 102 may be disposed between the X-ray source 101 and the splitting element 103. The monochromatizing unit 102 may be a combination of a monochromator and slits, or an X-ray multilayer mirror. In order to reduce blurring of an image caused by scattered X-rays from the attenuation unit 105, a grid used for radiography may be disposed between the attenuation unit 105 and the detector 106.

Figure 2:
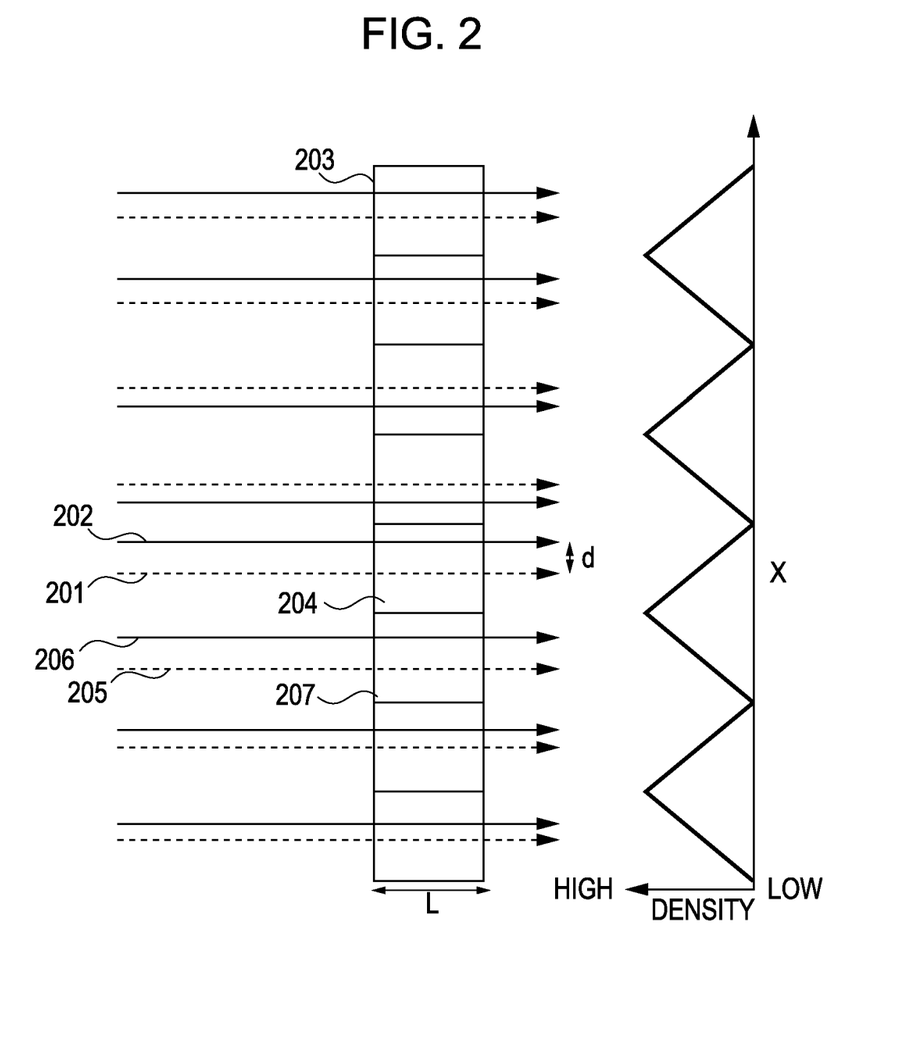
FIG. 2 is a schematic view of an attenuation unit included in the apparatus according to the first embodiment.

FIG. 2 is a partial schematic view of the attenuation unit 105. A reference X-ray 201 is an X-ray that has been split when the object 104 is not present. An X-ray 202 is an X-ray that has been refracted by the object 104.

As illustrated on the right-hand side of FIG. 2, the attenuation unit 105 includes attenuation elements 204 (first attenuation elements) and attenuation elements 207 (second attenuation elements) that are alternately arranged adjacent to one another. Each of the attenuation elements 204 has a linear density distribution with respect to the X direction (a direction perpendicular to incident X-rays). That is, each of the attenuation elements 204 has a density variation that changes the degree of absorption of X-rays. The higher the density, the less transparent the attenuation element 204 is to X-rays. In other words, the attenuation element 204 has an absorptance gradient that changes the absorption amount (transmission amount) of X-rays in accordance with the displacement of the X-rays. The reference X-rays 201 and 205 can respectively be incident on the middle positions of the attenuation elements 204 and 207 with respect to the X direction. The intensity $I_1$ of the reference X-ray 201 that has passed through the attenuation element 204 is expressed by equation (1).

$$I_1 = I_0 e^{-\left(\frac{\mu}{\rho}\right)\rho_1 L} \quad \text{[Math. 1]}$$

$I_0$ is the intensity of X-rays that have been spatially split by the splitting element 103, $\mu/\rho$ is the effective mass absorption coefficient of the attenuation element 204, $\rho_1$ is the density of the attenuation element 204 at a portion through which the reference X-ray 201 has passed, and L is the thickness of the attenuation element 204. The intensity $I_2$ of the X-ray 202 that has been refracted by the object 104 and passed through the attenuation element 204 is expressed by equation (2).

$$I_2 = I_0 A e^{-\left(\frac{\mu}{\rho}\right)\rho_2 L} \quad \text{[Math. 2]}$$

A is the X-ray transmittance of the object 104, and $\rho_2$ is the density of the attenuation element 204 at a portion of the attenuation element 204 through which the X-ray 202 has passed. From equations (1) and (2), the difference in the density of the attenuation element 204 with respect to the reference X-ray 201 and the X-ray 202 is expressed by equation (3).

$$\rho_1 - \rho_2 = \frac{1}{\left(\frac{\mu}{\rho}\right)L} \ln\left(\frac{I_2}{I_1 A}\right) \quad \text{[Math. 3]}$$

The attenuation element 207 (second attenuation element) is disposed adjacent to the attenuation element 204 (first attenuation element). The attenuation element 207 has a density distribution that is symmetrical to that of the attenuation element 204.

As with equation (3), the difference in the density of the attenuation element 207 (second attenuation element) with respect to the reference X-ray 205 and the X-ray 206 is expressed by equation (4).

$$\rho'_1 - \rho'_2 = \frac{1}{\left(\frac{\mu}{\rho}\right)L} \ln\left(\frac{I'_2}{I'_1 A}\right) \quad \text{[Math. 4]}$$

$\rho'_1$ is the density of the attenuation element 207 at a portion through which the reference X-ray 205 has passed, and $\rho'_2$ is the density of the attenuation element 207 at a portion through which the X-ray 206 has passed. $I'_1$ is the intensity of the reference X-ray 205 that has passed through the attenuation element 207, and $I'_2$ is the intensity of the reference X-ray 206 that has passed through the attenuation element 207.

Considering that the attenuation elements 204 and 207 have density distributions that are symmetrical to each other and assuming that the distance between the reference X-rays 201 and 205 is equal to the distance between the refracted X-rays 202 and 206, equation (5) is obtained.

$$\rho_1 - \rho_2 = -(\rho'_1 - \rho'_2) \quad \text{[Math. 5]}$$

The X-ray transmittance A of the object 104 can be calculated using equation (6) derived from equations (3), (4), and (5).

$$A = \sqrt{\frac{I_2 I'_2}{I_1 I'_1}} \quad \text{[Math. 6]}$$

That is, the X-ray transmittance A can be obtained from the intensity $I_1$ of the reference X-ray 201 and the intensity $I_2$ of the X-ray 202 that have passed through the attenuation element 204, and from the intensity $I'_1$ of the reference X-ray 205 and the intensity $I'_2$ of the X-ray 206 that have passed through the attenuation element 207.

By substituting X-ray transmittance A into equation (3) or (4), $\rho_1-\rho_2$ or $\rho'_1-\rho'_2$ can be obtained. Because the density distribution of the attenuation element is known, the displacement d of X-rays on the attenuation unit 105 can be obtained from the density difference. Otherwise, a table of the correspondence relation between the transmitted X-ray intensity and the displacement d can be stored in the calculating unit 107, storage, or the like. The displacement d can be estimated from the measured intensity using the data table. This data table can be prepared, for respective attenuation elements 204, by moving the attenuation unit 105 or the splitting element 103 and detecting the transmitted X-ray intensity at each of the positions. Also, in preparing the data table, a single slit having the same slit width as the splitting element 103 may be employed, and the transmitted X-ray intensity is detected at the respective positions of the attenuation elements 204.

That is, a displacement due to refraction caused by the object 104 can be obtained from a detected intensity.

In the example described above, the attenuation elements 204 and 207 have density distributions that are symmetric to each other. However it is not necessary that the density distributions be symmetric to each other. As shown in equation (5), the X-ray transmittance and the displacement can be obtained from the relationship between the density distributions of the two attenuation elements. That is, it is sufficient that the transmission amounts of the attenuation elements 204 and 207 change differently in the direction of a displacement of X-rays.

This method calculates the transmittance using the two attenuation elements and then obtains the displacement.

Therefore, a precise differential phase image or a precise phase image can be obtained even if an object absorbs a large amount of X-rays.

In this case, the spatial resolution is halved, because the differential phase image and the like are formed by using information about the intensities of X-rays that have passed through two regions of the attenuation element 204 and the attenuation element 207.

In order to suppress the reduction in the spatial resolution, in addition to the above-described measurement, measurement can be performed while moving the attenuation unit 105 or the object 104 in the X direction by the length of the attenuation element 204. Thus, information about the X-ray transmittance A corresponding to a position of the object 104 for which the displacement of the X-rays has been measured previously can be obtained.

By using the attenuation unit 105, information about the absorption effect of X-rays and information about the refraction effect of the X-rays can be independently obtained. Moreover, by using the attenuation unit 105, the displacement of X-rays that is equal to or smaller than the pixel size of the detector 106 can be detected, whereby the distance between the object and the detector can be reduced, so that the apparatus can be reduced in size.

Figure 3:
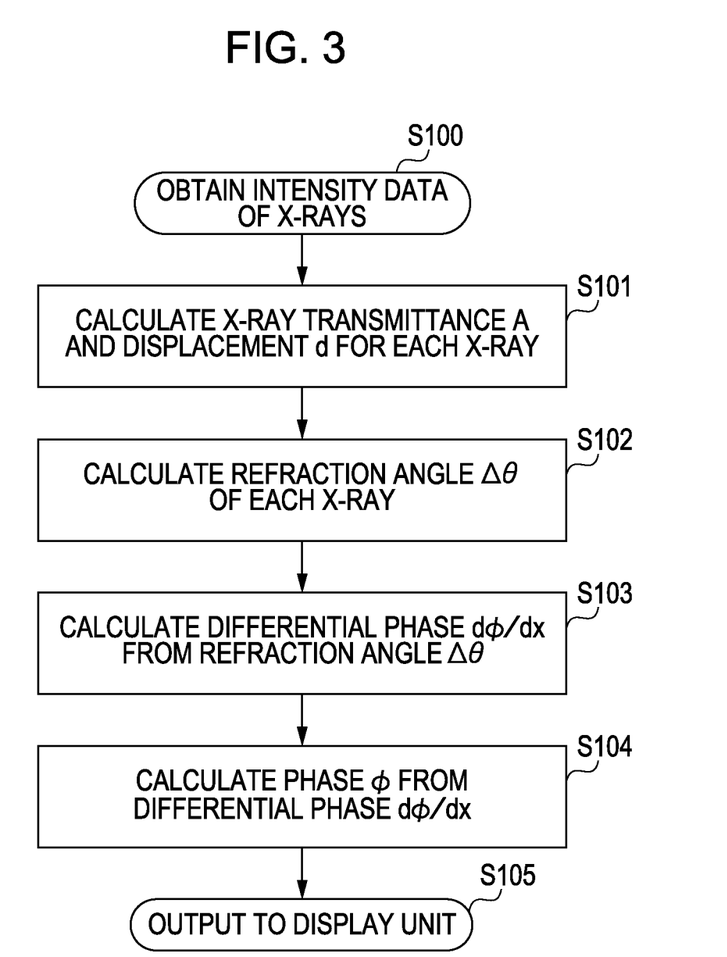
FIG. 3 is a flowchart of a process performed by a calculating unit included in the apparatus according to the first embodiment.

FIG. 3 is a flowchart of a process performed by the calculating unit 107. First, information about the intensity of each X-ray that has passed through the attenuation unit 105 is obtained (S100). Next, the X-ray transmittance A and the displacement d with respect to the reference X-ray 201 are calculated from the information about the intensity of each X-ray (S101). The refraction angle $\Delta\theta$ of each X-ray is expressed by equation (7) by using the displacement d and the distance Z between the object 104 and the attenuation unit 105.

$$\Delta\theta = \tan^{-1}\left(\frac{d}{Z}\right) \qquad \text{[Math. 7]}$$

Using equation (7), the refraction angle $\Delta\theta$ of each X-ray is calculated (S102). The refraction angle $\Delta\theta$ and the differential phase $d\phi/dx$ has the relationship expressed by equation (8).

$$\frac{d\phi}{dx} = \frac{2\pi}{\lambda}\Delta\theta \qquad \text{[Math. 8]}$$

$\lambda$ is the wavelength of the X-rays. For continuous X-rays, the wavelength refers to the effective wavelength. Using equation (8), the differential phase $d\phi/dx$ of each X-ray is calculated (S103). The differential phase $d\phi/dx$ is integrated in the X direction so as to calculate the phase $\phi$ (S104).

The transmittance image, the differential phase $d\phi/dx$, and the phase $\phi$, which have been calculated as described above, can be displayed on the display unit 108 (S105).

With this structure, a slight displacement within a small pixel of the detector 106 can be detected. Therefore, it is not necessary that the distance between the object 104 and the detector 106 be large, and the apparatus can be reduced in size. Moreover, an insensitive region does not exist, because the attenuation unit 105 is of a pass-through-type that does not have a region that blocks X-rays.

By increasing the distance between the object 104 and the detector 106, a smaller displacement of X-rays due to refraction can be measured.

With the above-described structure, because the phase shift is detected by using the refraction effect of X-rays, a differential phase image or an X-ray phase image with consideration of an absorption effect can be obtained without necessarily using highly coherent X-rays.

The above-described apparatus obtains a differential phase image or a phase image. However, a transmittance image obtained form absorption information may be displayed on the display unit 108.

In FIG. 2, the attenuation element has a density that changes continuously. However, the attenuation element may have a density that changes stepwise.

Second Embodiment

Figure 4:
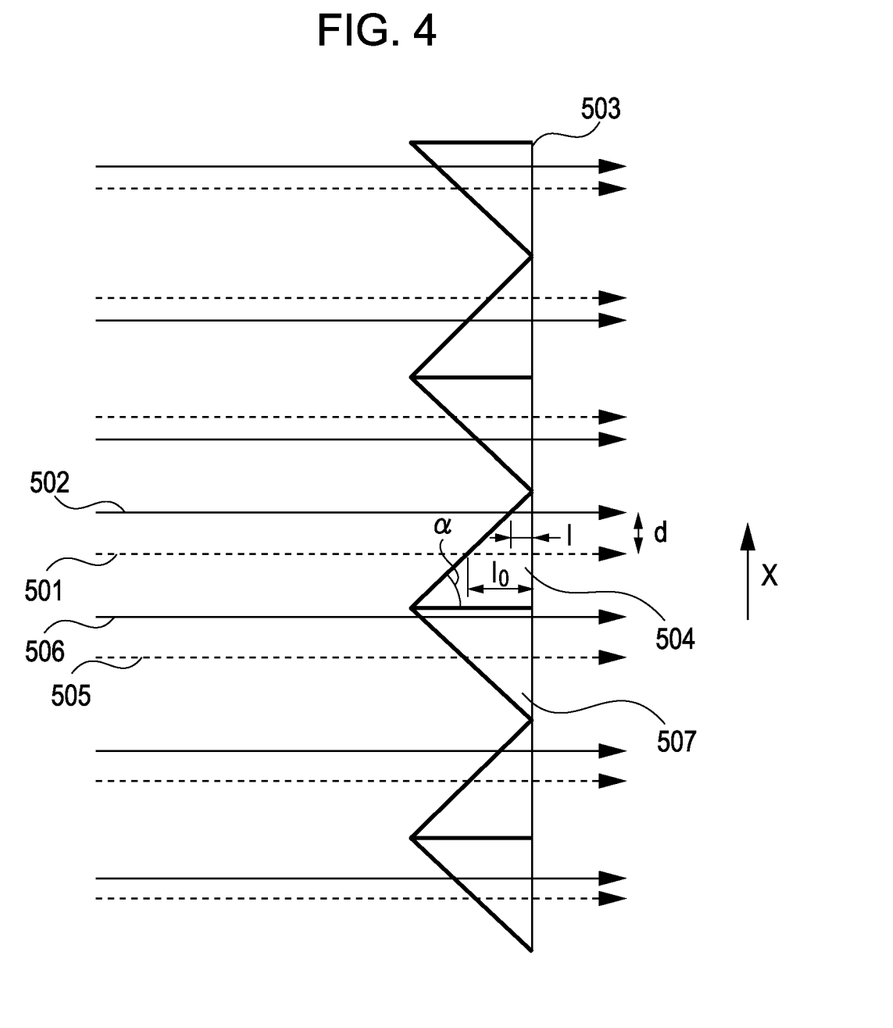
FIG. 4 is a schematic view of an attenuation unit included in an apparatus according to the second embodiment.

An apparatus according to a second embodiment includes an attenuation unit illustrated in FIG. 4 instead of the attenuation unit included in the first embodiment. The structure of the apparatus is the same as the first embodiment. The object 104 is irradiated with the X-rays that have been spatially split by the splitting element 103, and the X-rays that have passed through the object 104 are incident on the attenuation unit 105. FIG. 4 is a partial schematic view of the attenuation unit 105.

A reference X-ray 501 is an X-ray that has been split when the object 104 is not present, and an X-ray 502 is an X-ray that has been refracted by the object 104. Attenuation elements 504 (first attenuation elements) and attenuation elements 507 (second attenuation elements), which are triangular prism shaped, are disposed symmetrically. Similar attenuation elements may be made by processing a plate-shaped member.

Because the attenuation elements 504 are triangular prism shaped, the optical path lengths of X-rays that pass through the attenuation elements 504 change in the X direction. The intensity of the reference X-ray 501 that has passed through the attenuation element 504 is expressed by equation (9).

$$I_1 = I_0 e^{-\mu l_0} \qquad \text{[Math. 9]}$$

$I_0$ is the intensity of X-rays that have been spatially split by the splitting element 103, $\mu$ is the effective linear absorption coefficient of the attenuation element 504, and $l_0$ is the optical path length of the reference X-ray 501 in the attenuation element 504. The intensity of the X-ray 502 that has been refracted by the object 104 and passed through the attenuation element 504 is expressed by equation (10).

$$I_2 = I_0 A e^{-\mu l} \qquad \text{[Math. 10]}$$

A is the X-ray transmittance of the object 104, and l is the optical path length of the X-ray 502 in the attenuation element 504. Using equations (9) and (10) and the vertex angle $\alpha$ of the attenuation element 504, the displacement d on the attenuation unit 105 can be expressed by equation (11).

$$d = \frac{1}{\mu}\ln\left(\frac{I_2}{I_1 A}\right)\tan\alpha \qquad \text{[Math. 11]}$$

As with the above-described case, by considering the displacement d with respect to the attenuation element 507 (second attenuation element), the X-ray transmittance A of the object 104 can be calculated using equation (12).

$$A = \sqrt{\frac{I_2 I'_2}{I_1 I'_1}}$$ [Math. 12]

That is, the X-ray transmittance A can be obtained from the intensity $I_1$ of the reference X-ray 501 and the intensity $I_2$ of the X-ray 502 that have passed through the attenuation element 504, and from the intensity $I'_1$ of a reference X-ray 505 and the intensity $I'_2$ of an X-ray 506 that have passed through the attenuation element 507.

By substituting the X-ray transmittance A into equation (11), displacement d can be obtained. Without Equation (11), the displacement d can be estimated from the table as described in the first embodiment. In the above-described case, the vertex angles of the two attenuation elements are the same, and the attenuation elements are disposed symmetrically. However, the X-ray transmittance A and the displacement d can be obtained when the attenuation elements are not disposed symmetrically and the vertex angles of the two attenuation elements are not the same.

This method calculates the transmittance using the two attenuation elements and then obtains the displacement. Therefore, a precise differential phase image or a precise phase image can be obtained even if an object absorbs a large amount of X-rays.

In this case, the spatial resolution is halved, because the differential phase image and the like are formed by using information about the intensities of X-rays that have passed through two regions of the attenuation element 504 and the attenuation element 507.

In order to suppress the reduction in the spatial resolution, in addition to the above-described measurement, measurement can be performed while moving the attenuation unit 105 or the object 104 in the X direction by the length of the attenuation element 504. Thus, information about the X-ray transmittance A corresponding to the position of the object 104 for which the displacement of the X-rays has been measured previously can be obtained.

Because the attenuation element 504 is triangular prism shaped, the displacement d can be determined from the ratio of the intensity of the reference X-ray 501 to the intensity of the X-ray 502 at any position on the attenuation element 504. The X-rays that have passed through the attenuation unit 105 are detected by the X-ray detector 106.

As illustrated in FIG. 3, using the detected data, the calculating unit 107, which is similar to that of the first embodiment, calculates the transmittance A, the differential phase $d\phi/dx$, and the phase $\phi$. The results of the calculation can be displayed on the display unit 108.

With this structure, a slight displacement of X-rays within a small pixel of the detector 106 can be detected. Therefore, it is not necessary that the distance between the object 104 and the detector 106 be large, and the apparatus can be reduced in size. Moreover, a dead region does not exist, because the attenuation unit 105 is of a pass-through-type that does not have a region that blocks X-rays.

By increasing the distance between the object 104 and the detector 106, a smaller displacement of X-rays due to refraction can be detected.

With the above-described structure, because the phase shift is detected by using the refraction effect of X-rays, a differential phase image or an X-ray phase image with consideration of an absorption effect can be measured without necessarily using highly coherent X-rays.

The above-described apparatus obtains a differential phase image or a phase image. However, a transmittance image obtained form absorption information may be displayed on the display unit 108.

In FIG. 4, the attenuation element has a shape that changes continuously. However, the attenuation element may have a shape that changes stepwise.

Third Embodiment

An apparatus according to a third embodiment obtains a three-dimensional absorption distribution and a phase distribution by using the principle of computed tomography (CT).

Figure 5:
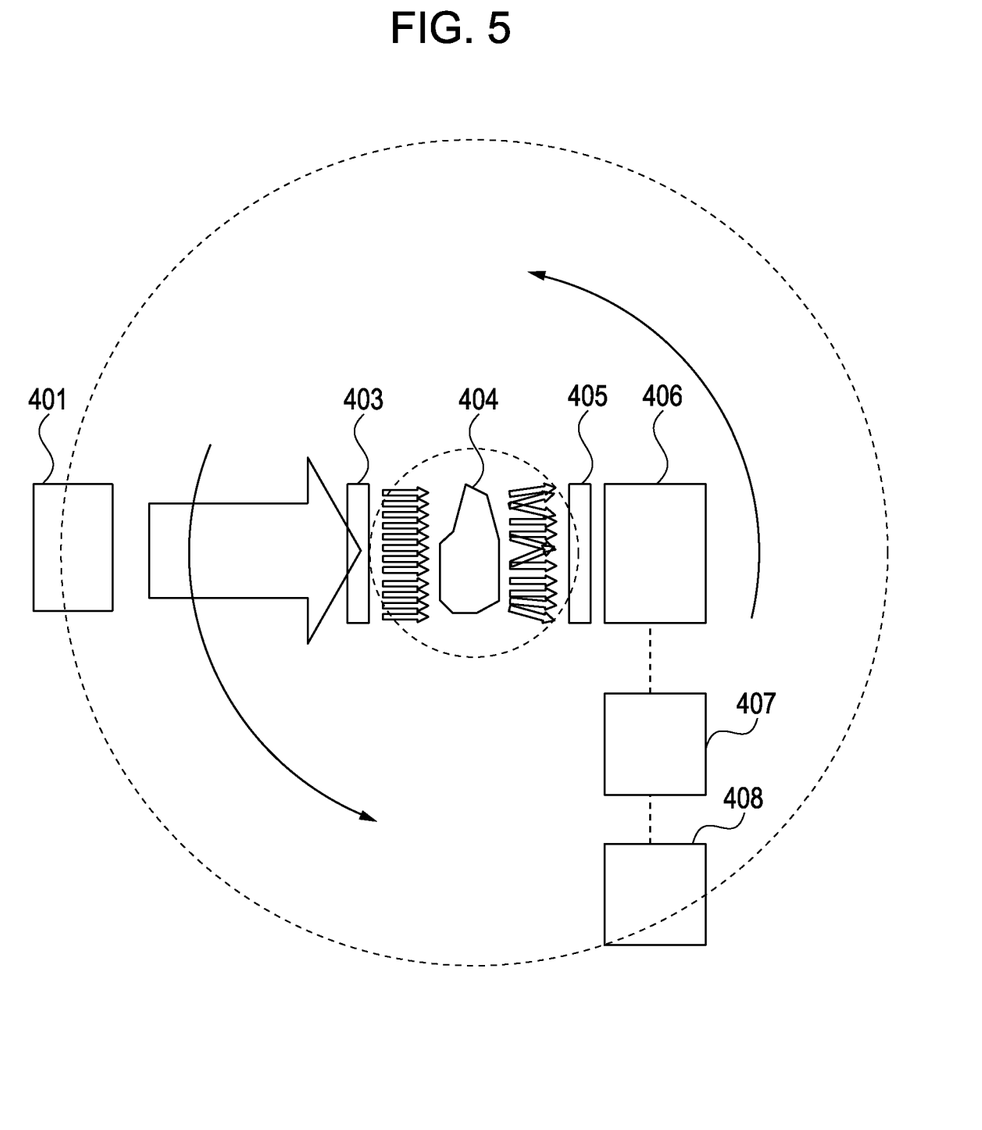
FIG. 5 is a schematic view of a CT apparatus according to a third embodiment.

FIG. 5 illustrates an apparatus according to the third embodiment. An X-ray source 401, a splitting element 403, an attenuation unit 405, and an X-ray detector 406 can be rotated around an object 404 by a movement unit in a synchronized manner. The splitting element 403 spatially splits X-rays, the object 404 is irradiated with the X-rays, and the X-rays that have passed through the object 404 are incident on the attenuation unit 405.

Owing to the attenuation unit 405, the amount of the X-rays that have been split and absorbed by the object 404 and small displacements of the X-rays due to refraction can be obtained. The X-rays that have passed through the attenuation unit 405 are detected by the X-ray detector 406. As with the first and second embodiments, imaging may be performed while moving the object 404 or the attenuation unit 405. Projection data of the object 404 can be obtained by performing imaging while the X-ray source 401, the splitting element 403, the attenuation unit 405, and the X-ray detector 406 are being rotated around the object 404 in a synchronized manner. The object 404 may be rotated so as to obtain the projection data, instead of rotating the splitting element 403, the attenuation unit 405, and the X-ray detector 406.

Figure 6:
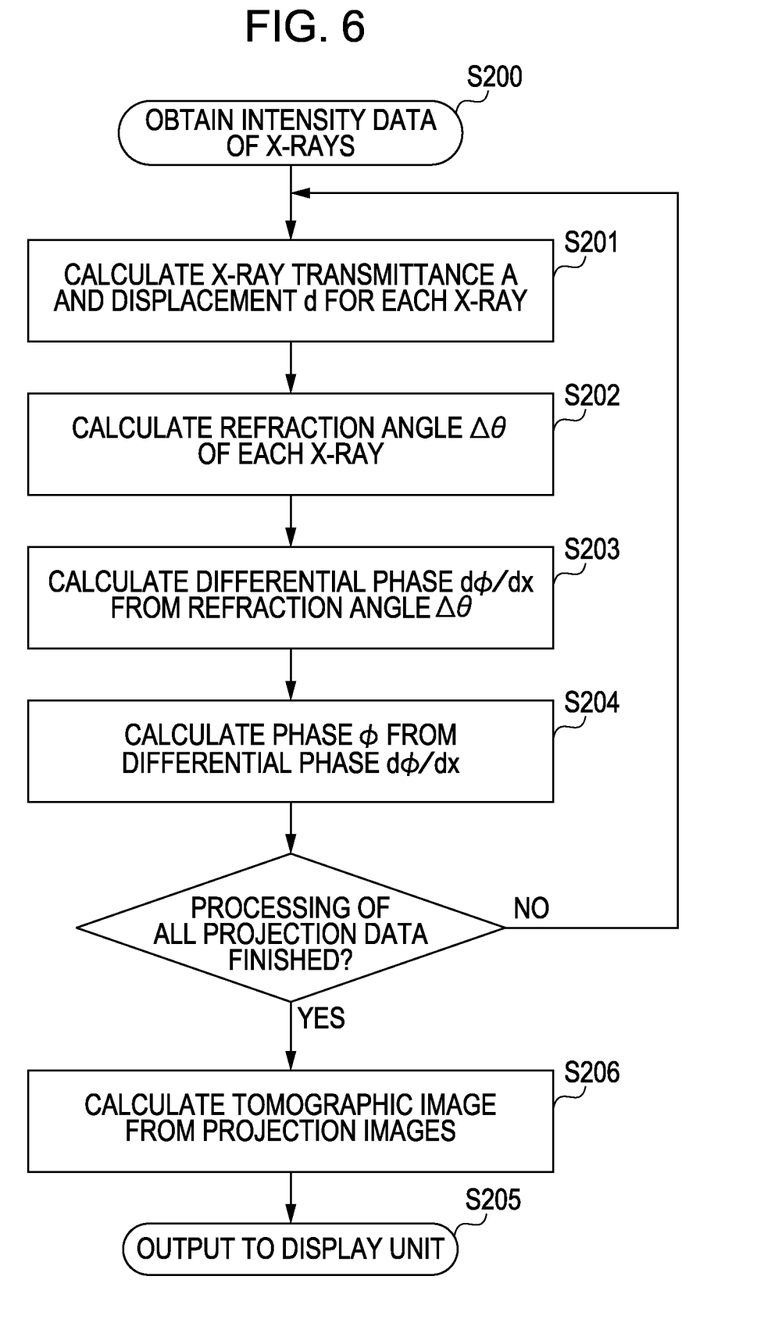
FIG. 6 is a flowchart of a process performed by a calculating unit included in an apparatus according to the third embodiment.

FIG. 6 is a flowchart of a process performed by a calculating unit 407. First, information about the intensity of each X-ray that has passed through the attenuation unit 405 is obtained (S200).

Next, the X-ray transmittance A is obtained from the information about the intensity of each X-ray, and the displacement d with respect to the reference X-ray 501 is calculated (S201). Using the displacement d and the distance Z between the object 404 and the attenuation unit 405, the refraction angle ($\Delta\theta$) of each X-ray is calculated (S202). The differential phase $d\phi/dx$ of each X-ray is calculated from the refraction angle $\Delta\theta$ (S203).

The differential phase $d\phi/dx$ is integrated in the X direction so as to calculate the phase $\phi$ (S204).

The series of operations (S201 to S204) are performed for all projection data. By applying an image reconstruction method (for example, a filter backprojection method) of computed tomography to the absorption images and the phase images of all the projection data, tomographic images are obtained (S206). The tomographic images can be displayed on a display unit 408 (S205).

With this structure, the CT apparatus can be reduced in size. Moreover, because the apparatus uses the refraction effect of X-rays, the CT apparatus can nondestructively obtain a three-dimensional linear absorption coefficient image and a phase image of an object without necessarily using highly coherent X-rays.

Other Embodiments

Each of the above-described embodiments includes attenuation elements each having an absorptance gradient (transmittance gradient) in one direction. However, the attenuation element may have an absorptance gradient (transmittance gradient) in more than one directions. For example, by providing the attenuation element with absorption gradients in the X and Y directions, two-dimensional phase gradient can be measured. Examples of a shape having gradients in the X and Y directions include a pyramidal shape and a conical shape.

Alternatively, a two-dimensional phase gradient can be detected by using an attenuation unit including two types of attenuation elements arranged in a plane, one type of the attenuation elements each having a gradient in the X direction and the other type of the attenuation elements each having a gradient in Y direction.

As a further alternative, attenuation elements each having gradients in the X direction and in the Y direction may be stacked on top of one another.

As described above, the X-ray imaging apparatus according to an embodiment the present invention includes a first element configured to obtain first intensity data and a second element configured to obtain second intensity data, the second element being disposed adjacent to the first element. The X-ray imaging apparatus further includes a calculation unit that calculates the amount of phase shift of X-rays using the first and second intensity data. The calculation unit obtains the amount of phase shift of X-rays caused by the object using the first or second intensity data on the basis of the X-ray transmittance obtained by the calculation unit.

The X-ray imaging method according to an embodiment of the present invention includes obtaining first intensity data using a first element, obtaining second intensity data using a second element, the second element being disposed adjacent to the first element, and obtaining an X-ray transmittance of an object using the first and second intensity data. The method further includes obtaining the amount of phase shift of X-rays using the first or second intensity data on the basis of the X-ray transmittance that has been obtained.

EXAMPLE

Figure 7:
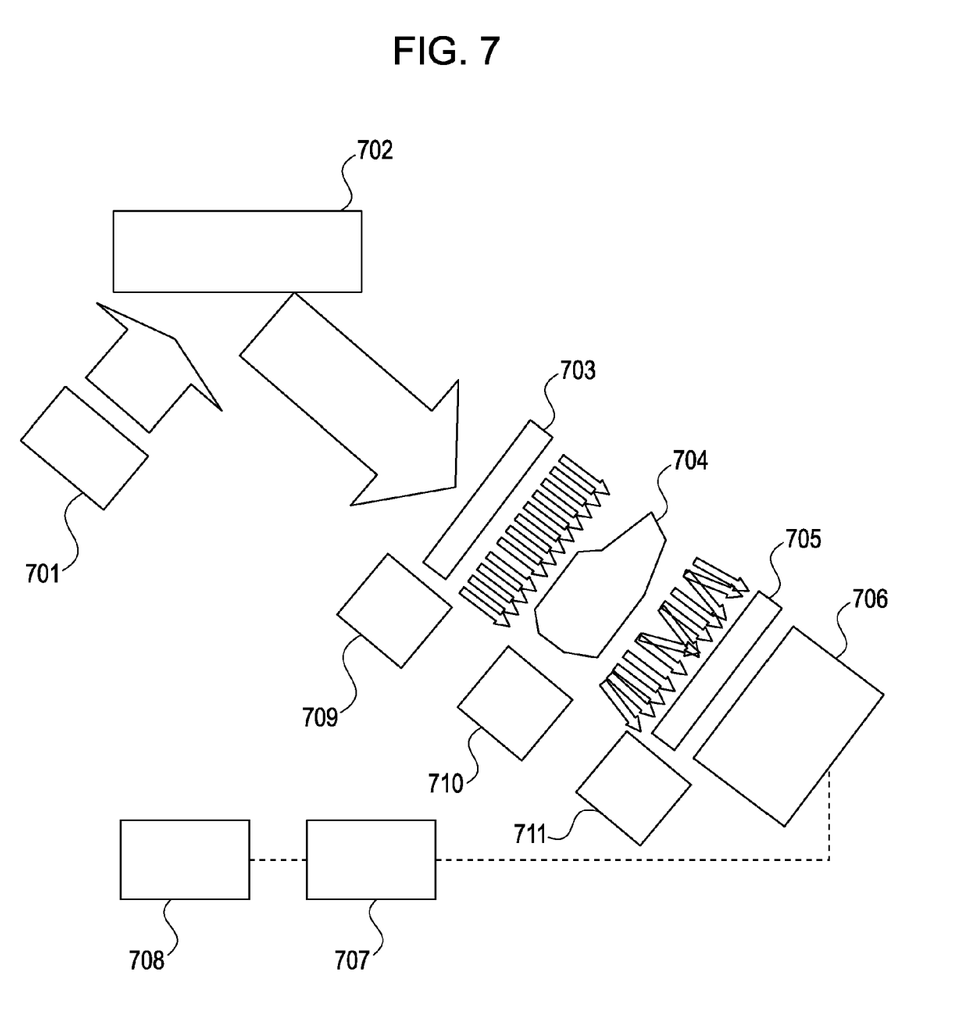
FIG. 7 is a schematic view of an apparatus described as an example.

FIG. 7 is a schematic view of an apparatus described as an example.

As an X-ray generator, an X-ray source 701 that is a Mo target rotating-cathode-type X-ray generating apparatus was used. A monochromator 702 made of high orientation pyrolytic graphite (HOPG) was used as a monochromatizing unit of X-rays so as to extract characteristic X-rays of Mo.

A splitting element 703 was disposed at a position that is 100 cm away from the X-ray source. The X-rays that had been monochromatized by the monochromator 702 were spatially split by the splitting element 703. As the splitting element 703, a tungsten (W) plate that has a thickness 100 μm and slits arranged therein, each of the slits having a width of 40 μm, was used. The intervals between the slits were 150 μm on an attenuation unit 705. Besides W, materials such as Au, Pb, Ta, and Pt can be used.

An object 704 was irradiated with X-rays split by the splitting element 703. The attenuation unit 705 was disposed at a position that was 50 cm away from the object 704. The X-rays that had passed through the object 704 were incident on the attenuation unit 705. Movement units 709, 710, and 711 using stepper motors were respectively provided to the splitting element 703, the object 704, and the attenuation unit 705.

The attenuation unit 705 had a structure in which triangular prisms made of Ni are arranged on a carbon substrate having a thickness of 1 mm. The length of a side of a triangle that is a section of each triangular prism was 300 μm, and the height of the triangular prism was 75 μm. Using an X-ray detector 706, which serves as a detecting unit and is disposed right behind the attenuation unit 705, the intensity of X-rays that have passed through the attenuation unit 705 was detected. Subsequently, the attenuation unit 705 was moved by 150 μm with the movement unit 711 in the direction in which the triangular prisms were arranged, and a similar measurement was performed. As the X-ray detector 706, a flat panel detector having a pixel size of 50 μm×50 μm was used. The sum of the intensities of the X-rays for three pixels arranged in the direction in which the triangular prisms were arranged was used as the intensity of the X-rays for one attenuation element.

Using a change in the intensity of each X-ray from the intensity obtained when similar imaging was performed without the object 704, a calculating unit 707 calculated the X-ray transmittance A of the object 704, so that a transmittance image was obtained. The calculating unit 707 also calculated the displacement d using equation (8) and the refraction angle $\Delta\theta$ using equation (4).

The amount of differential phase was calculated from the refraction angle $\Delta\theta$ using equation (5), and a phase distribution image was obtained by spatially integrating the amount of differential phase.

The X-ray transmittance image, the X-ray differential phase image, and the X-ray phase image, which had been calculated by the calculating unit 707, were displayed on a PC monitor that served as a display unit 708.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-006862 filed Jan. 15, 2009 and No. 2009-264411 filed Nov. 19, 2009, which are hereby incorporated by reference herein in their entirety.

| Reference Signs List | |
|---|---|
| 101 | X-ray source |
| 102 | monochromatizing unit |
| 103 | splitting element |
| 104 | object |
| 105 | attenuation unit |
| 106 | detector |
| 107 | computing unit |
| 108 | display unit |
| 109 | movement unit |
| 110 | movement unit |
| 111 | movement unit |
| 201 | reference X-ray |
| 202 | X-ray |
| 203 | attenuation unit |
| 204 | attenuation element |
| 205 | reference X-ray |
| 206 | X-ray |
| 207 | attenuation element |

The invention claimed is:
1. An X-ray imaging apparatus comprising:
a splitting element that spatially splits X-rays generated by an X-ray generator;
a first attenuation element on which X-rays split by the splitting element and passed through an object are incident;

a second attenuation element on which X-rays split by the splitting element and passed through the object are incident, the second attenuation element being disposed adjacent to the first attenuation element; and a detecting unit configured to detect intensities of X-rays that have passed through the first attenuation element and the second attenuation element, wherein the first attenuation element and the second attenuation element are configured so that a transmission amount of X-rays continuously changes in accordance with a position at which the X-rays are incident, and wherein the first attenuation element and the second attenuation element are different from each other with respect to an amount of change or a characteristic of change in a transmission amount of X-rays in a direction of a displacement of the X-rays.

2. The X-ray imaging apparatus according to claim 1, further comprising:

a calculating unit configured to calculate a differential phase image or a phase image of an object using an X-ray transmittance that is calculated from the intensities of X-rays detected by the detecting unit.

3. The X-ray imaging apparatus according to claim 2, wherein the calculating unit calculates a transmittance image of the object from the intensities of X-rays detected by the detecting unit.

4. The X-ray imaging apparatus according to claim 1, wherein a thickness of the first or second attenuation element continuously changes in a direction perpendicular to a direction of X-rays incident on the first or second attenuation element.

5. The X-ray imaging apparatus according to claim 4, wherein the first or second attenuation element is a structure having a shape of a triangular prism.

6. The X-ray imaging apparatus according to claim 1, wherein a density of the first or second attenuation element continuously changes in a direction perpendicular to a direction of X-rays incident on the first or second attenuation element.

7. A method of X-ray imaging used in an X-ray imaging apparatus, the method comprising:

generating X-rays;

spatially splitting the X-rays;

making X-rays that have been spatially split be incident on a first attenuation element and a second attenuation element, the second attenuation element being disposed adjacent to the first attenuation element;

detecting intensities of X-rays that have passed through the first attenuation element and the second attenuation element; and calculating a differential phase image or a phase image of an object using an X-ray transmittance, the X-ray transmittance being calculated from the intensities of X-rays that have been detected, wherein the first attenuation element and the second attenuation element are configured so that a transmission amount of X-rays continuously changes in accordance with a position at which the X-rays are incident, and wherein the first attenuation element and the second attenuation element are different from each other with respect to an amount of change or a characteristic of change in the transmission amount of X-rays in a direction of a displacement of the X-rays.

8. An X-ray imaging apparatus comprising:

a splitting element that spatially splits X-rays generated by an X-ray generator into first X-rays and second X-rays in a first direction perpendicular to a beam axis of X-rays;

a first attenuation element on which the X-rays split by the splitting element and passed through an object are incident;

a second attenuation element on which the X-rays split by the splitting element and passed through the object are incident, the second attenuation element being disposed in the first direction adjacent to the first attenuation element; and a detecting unit configured to detect first intensities of the first X-rays that have passed through the first attenuation element and second intensities of the second X-rays that have passed through the second attenuation element, wherein the first attenuation element and the second attenuation element are configured so that their respective X-ray transmission changes in the first direction in accordance with a position on the respective attenuation element, and wherein the first attenuation element and the second attenuation element are different from each other with respect to an amount of change or a characteristic of change of the respective X-ray transmission in the first direction.

9. The X-ray imaging apparatus according to claim 8, further comprising:

a calculating unit configured to calculate a differential phase image or a phase image of an object from the first and second intensities.

10. The X-ray imaging apparatus according to claim 9, wherein the calculating unit is configured to calculate a transmittance image of the object from the first and second intensities.

11. The X-ray imaging apparatus according to claim 8, wherein a thickness of the first or second attenuation element changes in the first direction.

12. The X-ray imaging apparatus according to claim 11, wherein the first or second attenuation element is a structure having a shape of a triangular prism.

13. The X-ray imaging apparatus according to claim 8, wherein a density of the first or second attenuation element changes in the first direction.

* * * * *